United States Patent
Nash et al.

(10) Patent No.: US 9,655,623 B2
(45) Date of Patent: May 23, 2017

(54) SYSTEM FOR CLOSING A WOUND

(71) Applicants: Alan E. Nash, Gastonia, NC (US);
Zachary T. Amodt, Woodinville, WA (US)

(72) Inventors: Alan E. Nash, Gastonia, NC (US);
Zachary T. Amodt, Woodinville, WA (US)

(73) Assignee: Alan E. Nash, Gastonia, NC (US)

(*) Notice: Subject to any disclaimer, the term of this patent is extended or adjusted under 35 U.S.C. 154(b) by 13 days.

(21) Appl. No.: 14/174,885

(22) Filed: Feb. 7, 2014

(65) Prior Publication Data
US 2014/0236227 A1 Aug. 21, 2014

Related U.S. Application Data

(60) Provisional application No. 61/765,385, filed on Feb. 15, 2013.

(51) Int. Cl.
A61B 17/08 (2006.01)
A61D 1/00 (2006.01)

(52) U.S. Cl.
CPC ...... *A61B 17/085* (2013.01); *A61B 2017/081* (2013.01); *A61B 2017/086* (2013.01)

(58) Field of Classification Search
CPC ..... A61B 17/04; A61B 17/0466; A61B 17/08; A61B 17/085; A61B 2017/0496; A61B 2017/086; A61B 2017/088
See application file for complete search history.

(56) References Cited

U.S. PATENT DOCUMENTS

| 3,971,384 | A |   | 7/1976  | Hasson |
|-----------|---|---|---------|--------|
| 4,038,989 | A |   | 8/1977  | Romero Sierra |
| 4,526,173 | A | * | 7/1985  | Sheehan ............ A61B 17/085 606/216 |
| 4,535,772 | A | * | 8/1985  | Sheehan ..................... 606/218 |
| 4,780,168 | A |   | 10/1988 | Beisang et al. |
| 4,905,681 | A |   | 3/1990  | Glascock |
| 5,000,741 | A |   | 3/1991  | Kalt |
| D333,193  | S |   | 2/1993  | Archambault |

(Continued)

OTHER PUBLICATIONS

Moris Topaz et al., "The TopClosure® 3S System, for skin stretching and a secure wound closure", Eur J Plast Surg (2012) 35:533-543.

(Continued)

*Primary Examiner* — Melanie Tyson
(74) *Attorney, Agent, or Firm* — Hammer & Associates, P.C.

(57) ABSTRACT

A system for wound closure has at least two closure elements. One closure element is detachably tethered to another closure element. Each closure element includes: a base member with an integral strap hingably connected to the base member, and a lock member slidably disposed on the strap and being lockable on the strap. Alternatively, the base member defines a plane and the strap being affixed to the base member at an angle to the plane. The system may further include a wound covering disposed between the straps and the wound. The wound covering may be a laminate having at least two layers; a first layer is a moisture impervious layer adapted to contain body heat, and a second hydrophilic layer is adapted to retain moisture.

22 Claims, 6 Drawing Sheets

(56) References Cited

U.S. PATENT DOCUMENTS

| | | |
|---|---|---|
| 5,259,835 A | 11/1993 | Clark et al. |
| 5,439,469 A | 8/1995 | Heaven et al. |
| 5,497,788 A | 3/1996 | Inman et al. |
| 5,630,430 A | 5/1997 | Shultz et al. |
| 5,944,562 A | 8/1999 | Christensson |
| D424,699 S | 5/2000 | Allen |
| 6,293,281 B1 | 9/2001 | Shultz et al. |
| 6,293,917 B1 | 9/2001 | Augustine et al. |
| 6,343,604 B1 | 2/2002 | Beall |
| 7,182,763 B2 | 2/2007 | Nardella |
| 7,361,185 B2 | 4/2008 | O'Malley et al. |
| 7,605,299 B2 | 10/2009 | Zocher |
| D623,740 S | 9/2010 | Harris et al. |
| 7,972,362 B2 | 7/2011 | Wilke et al. |
| 7,981,136 B2 | 7/2011 | Weiser |
| D652,145 S | 1/2012 | Topaz |
| 2003/0163160 A1* | 8/2003 | O'Malley ............... A61B 17/08 606/213 |
| 2007/0021779 A1 | 1/2007 | Garvin et al. |
| 2009/0036922 A1* | 2/2009 | Riskin .................. A61B 17/083 606/215 |
| 2010/0137817 A1* | 6/2010 | Hardman et al. ............ 604/290 |
| 2010/0228287 A1 | 9/2010 | Jeekel et al. |
| 2011/0166492 A1 | 7/2011 | Holm |

OTHER PUBLICATIONS

Woundcare Technologies, "Expanding Your Clinical Options"; DERMAClose RC, Continuous External Tissue Expander, Slide Presentation.

\* cited by examiner

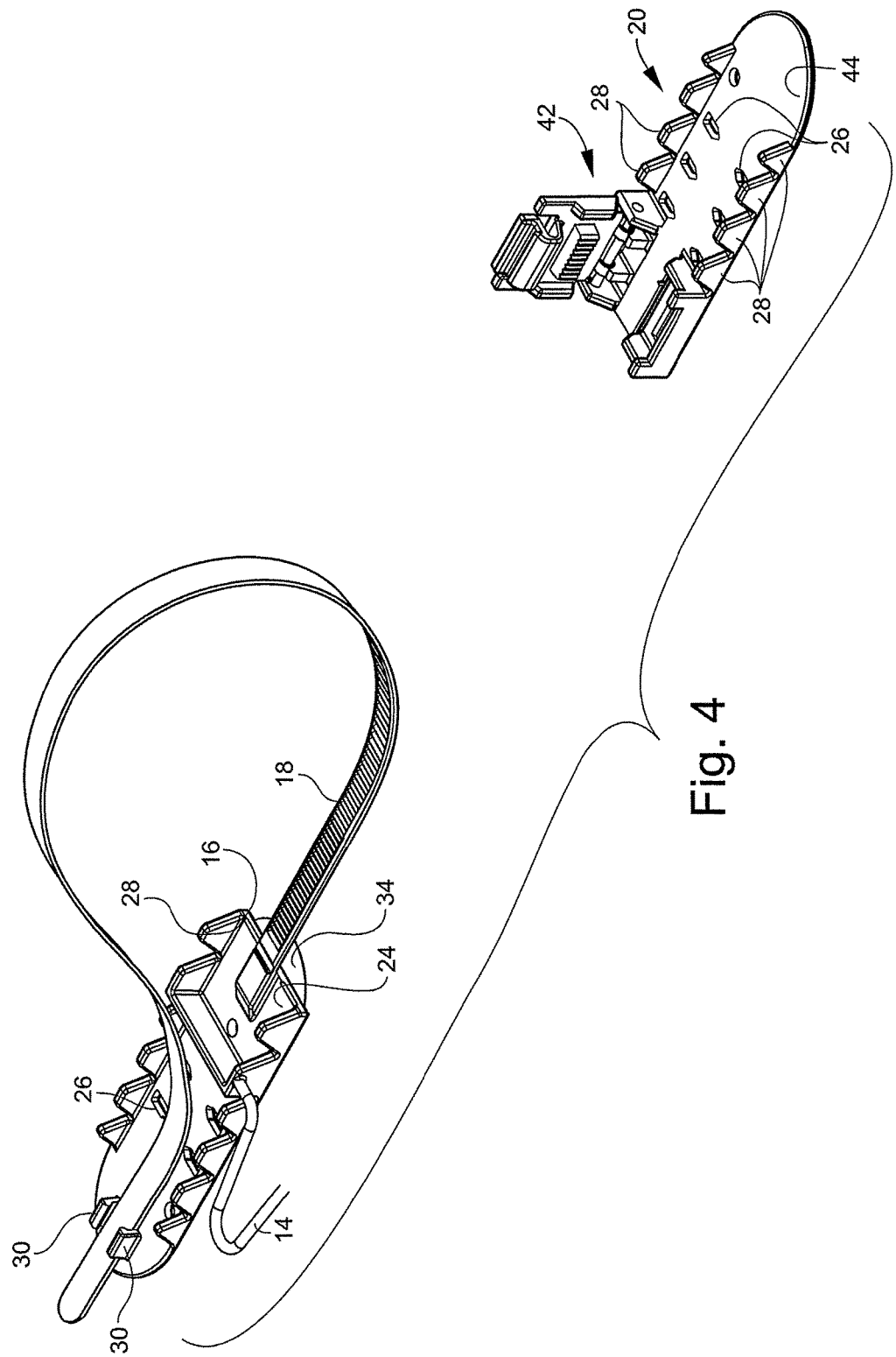

SYSTEM FOR CLOSING A WOUND

RELATED APPLICATION

This application claims the benefit of co-pending U.S. provisional application No. 61/765,385 filed Feb. 15, 2013, which is incorporated herein by reference.

FIELD OF THE INVENTION

This invention is directed to a system and method for closing a wound.

BACKGROUND OF THE INVENTION

Traumatic injuries typically occur away from medical facilities. Thus, the victim must be transported from the site where the injury occurred, such as a battlefield or a roadside, to the medical facility for treatment. During this 'short term' period, for example, transportation from the site to the facility, it may be best to keep the wound closed, as much as possible, and even covered, if possible, to prevent, for example, ingress of contaminants, or to facilitate treatment.

Two such devices have been proposed, they are discussed below.

U.S. Pat. No. 3,971,384 discloses a suture less closure device. The device has a tie strip with an anchor affixed at one end of the strip and a slide lockably engaged on the strip. The anchor is affixed to the skin on one side of the incision and the slide is affixed to the skin on the other side on the other side of the incision. The incision is closed by pulling the strip through the slide and locking the strip in the slide.

U.S. Design Patent No. D652145 discloses a wound closure device. The device has two wound closure clips and a strip therebetween.

While these devices may be used in the situations discussed above, improvements are needed. Those improvements include, but are not limited to, ease of operation, compactness, reduced weight, fewer pieces, rapid deployment, and versatility, to mention a few.

Accordingly, the invention, discussed below, addresses and improves upon, at least, the issues mentioned above.

SUMMARY OF THE INVENTION

A system for wound closure has at least two closure elements. One closure element is detachably tethered to another closure element. Each closure element includes: a base member with an integral strap hingably connected to the base member, and a lock member slidably disposed on the strap and being lockable on the strap. Alternatively, the base member defines a plane and the strap being affixed to the base member at an angle to the plane. The system may further include a wound covering disposed between the straps and the wound. The wound covering may be a laminate having at least two layers; a first layer is a moisture impervious layer adapted to contain body heat, and a second hydrophilic layer is adapted to retain moisture.

DESCRIPTION OF THE DRAWINGS

For the purpose of illustrating the invention, there is shown in the drawings a form that is presently preferred; it being understood, however, that this invention is not limited to the precise arrangements and instrumentalities shown.

FIG. 2A is an enlarged view of a portion of the embodiment shown in FIG. 2.

FIG. 4 is an illustration of the inventive system with the strap folded and releasably affixed to the base member and the lock mechanism of the lock member in an open position.

DESCRIPTION OF THE INVENTION

Figure 1:
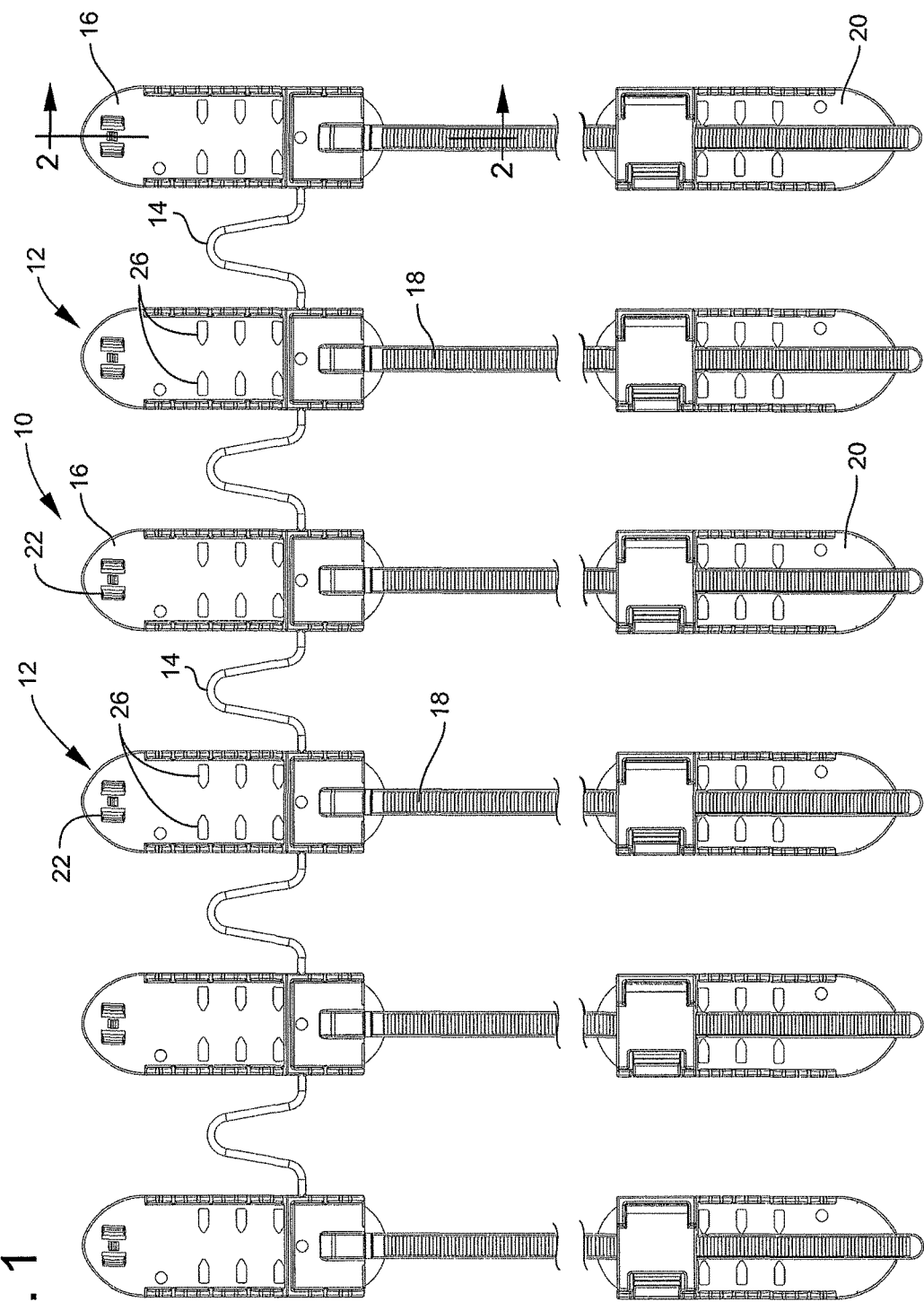
FIG. 1 is an illustration of one embodiment of the system for closure of a wound.

Referring to the drawings, where like elements have like numerals, there is shown in FIG. 1 an embodiment of the system for closure of a wound 10, for example, short term closure. Generally, system 10 comprises a closure element 12. In one embodiment, several closures elements 12 may be joined together via a tether 14. But, closure elements 12 may be independent, i.e., not tethered. Several, as used herein, may mean at least two, but may include up to 12, or any whole number between 2 and 12.

The tether 14 may be breakable or cuttable, so that the number of closures 12 may be tailored to a suitable number for closure of the wound. Tether 14 may be positioned on an upper portion of the closure elements 12, so that the tether 14 does not touch the skin.

The system 10 may be made of one or more injection moldable thermoplastic materials, alone or in combination. Such thermoplastic materials include, but are not limited to, polyolefins (for example, polyethylene and polypropylene), polyesters (for example, polyethylene terephthalate), polyamides (for example, nylon), or the like.

Closure element 12 generally includes a base member 16, a strap 18, and a lock member 20. The base member 16 may be integral with the strap 18. The lock member 20 may be slidably and/or removably engaged with strap 18.

Referring to FIGS. 1-4, the base member 16 will be discussed in greater detail hereinafter. Base member 16 generally includes a strap fastener 22 and a bottom plate 24. Base member 16 optionally includes at least one pair of staple holes 26 through the bottom plate 24. Any number of pairs of staple holes may be used, for example, 1-4 pairs of staple holes including any whole number between 1 and 4. The staple holes 26 may be used so that the base member may be stapled to the skin surrounding the wound. The base member may also optionally include at least one pair of staple guides (e.g., teeth) 28, for example, upstanding from the lateral edges of the bottom plate 24. Additionally, the staple guides 28 allow the base member 16 to be more flexible therebetween. Any number of pairs of staple guides may be used, for example, 1-6 pairs of staple guides including any whole number between 1 and 6.

As shown in FIG. 4, strap fastener 22 may be used to releasably secure strap 18, so that the strap 18 may be held away for the wound. Strap fastener 22 may be any mechanism that can releasably hold strap 18. The strap fastener 22 may be generally located on the base member 16 at an end of the bottom plate 24 distal the strap 18. In one embodiment, shown in FIGS. 1, 2, and 4, strap fastener 22 may comprise a pair of lateral clips 30, each clip 30 spaced from the other so as to releasably secure strap 18 therebetween. The strap fastener 22 may optionally include strap engagement member 31. Strap engagement member 31 working with clips 30 may more securely hold the folded strap 18 in strap fastener 22. In another embodiment (not shown), strap fastener may be a post with mushroom head upstanding from bottom plate 24 for releasable engagement with one or more holes (not shown) through the strap 18.

Referring to FIG. 2A, base member 16 may include an adhesive 32 for releasably securing base member 16 to the skin adjacent the wound. In one embodiment, the adhesive 32 may be affixed to a bottom surface of the bottom plate 24. Adhesive 32 may be any adhesive suitable for releasably adhering the base member 16 to the skin adjacent the wound. The adhesive 32 may be a hydrocolloid dressing (for example, commercially available under such tradenames as Duoderm, Granuflex, Ultec, and 3M Tegaderm Hydrocolloid) and/or pressure sensitive adhesive. In one embodiment, the adhesive 32 covers all or a portion of the bottom surface of bottom plate 24. In one embodiment, the adhesive 32 may be protected, prior to use, by a release layer 34. In another embodiment, adhesive 32 may include a mesh (not shown) throughout the adhesive 32 and may extend beyond the peripheral edge of the adhesive 32.

Figure 2:
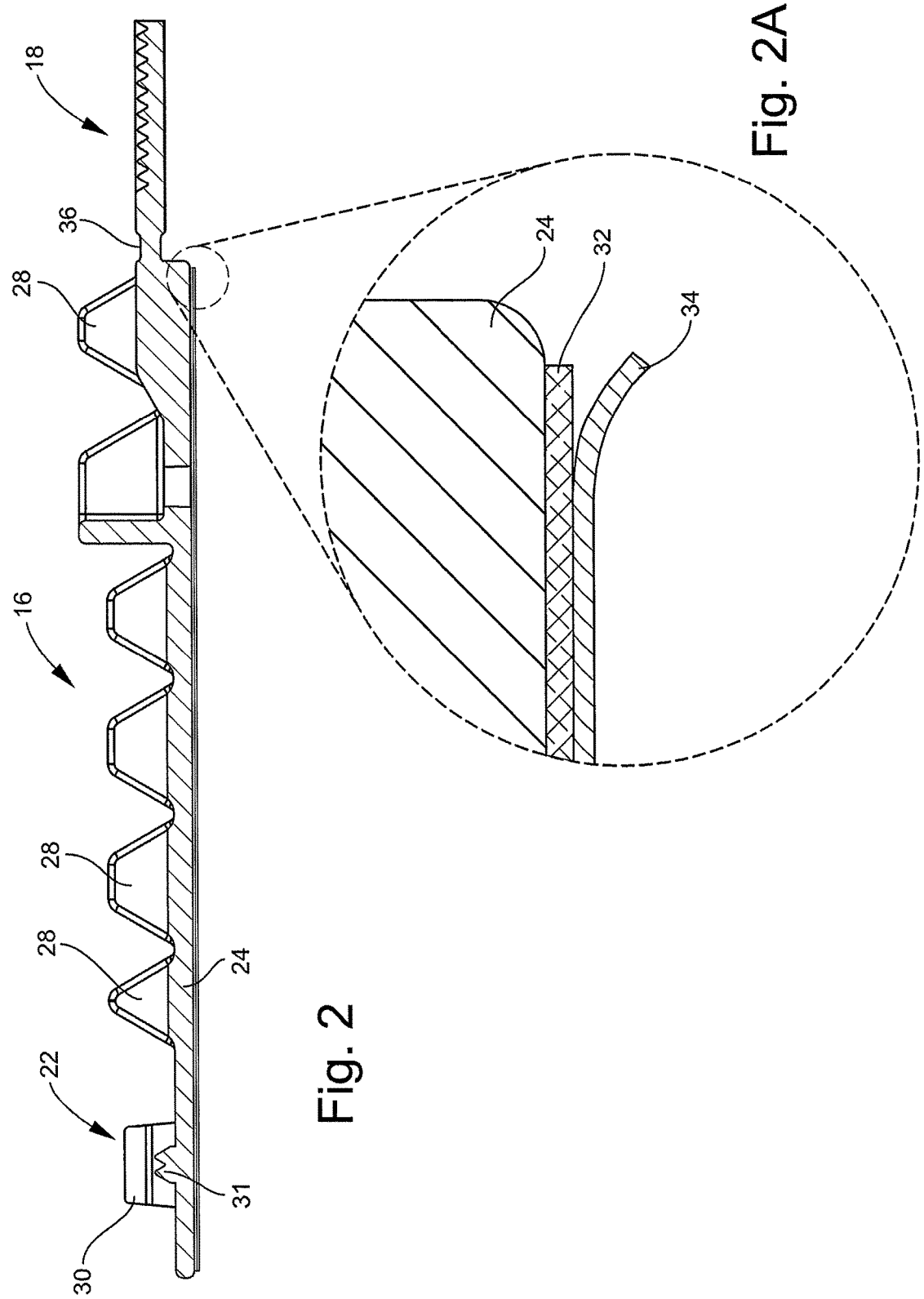
FIG. 2, taken generally along section lines 2-2 of FIG. 1, is an embodiment of the base member.
Figure 3:
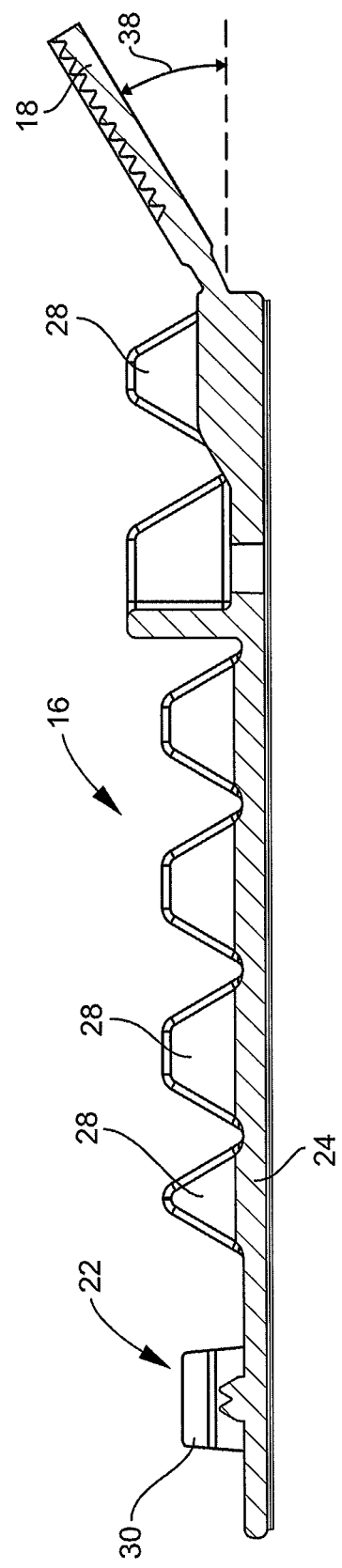
FIG. 3, taken generally along section lines 2-2 of FIG. 1, is another embodiment of the base member.

The base member 16 may be integral with strap 18. Integral, as used herein, may refer to the base member 16 and the strap 18 being molded as a single unit. The joint between the base member 16 and strap 18 should be flexible (i.e., capable of bending to allow fastening of the free end of the strap 18 to the base member 16 as shown in FIG. 4). The strap 18 may be hingably connected with the base member 16. In one embodiment, see FIG. 2, a hinge 36 joins the base member 16 with strap 18. Hinge 36, as shown in FIG. 2, may be formed by a thinning of material between the base member 16 and strap 18 (e.g., a living hinge). In another embodiment, see FIG. 3, the strap 18 is joined to the base member 16 at an angle 38. Angle 38 may be any angle greater than 0° and less than 90°. The angle 38 may be in the range of 10°-45°, or 15°-35°. In one embodiment, the angle 38 may be about 30°.

Strap 18, see FIGS. 1, 4, 5A, and 5B, is a elongated member extending away from the base member 16. The strap 18 is flexible. The strap may have a plurality of teeth 40 along a surface of strap 18 (for example, the upper surface). These teeth 40, in one aspect of the invention, may work with strap engagement member 31 of the strap fastener 22 (discussed above); and in another aspect of the invention, these teeth 40 may engage with strap engagement member 54 to hold the strap 18 fast in locking mechanism 42 (discussed below). The strap 18 may be any length. In one embodiment, the length may range from 12 inches to 36 inches. Strap 18 may be severable. For example, the strap may be severed (for example, with a knife or scissors) along its length so that the strap length may be tailored to a suitable length for closure of the wound. In one embodiment (not shown), the strap 18 may include one or more notches at regular intervals (for example, 1 or 2 inches) along the length of the strap 18 to facilitate severability. The notch may run across the width of the strap 18 (i.e., generally perpendicular to the longitudinal axis of the strap 18) and may be an area of the strap that may be generally thinner in depth than other areas of the strap, so that the notch acts as a guide for a knife to facilitate strap cutting in the dark as may be necessary under battle field conditions.

Figure 5A:
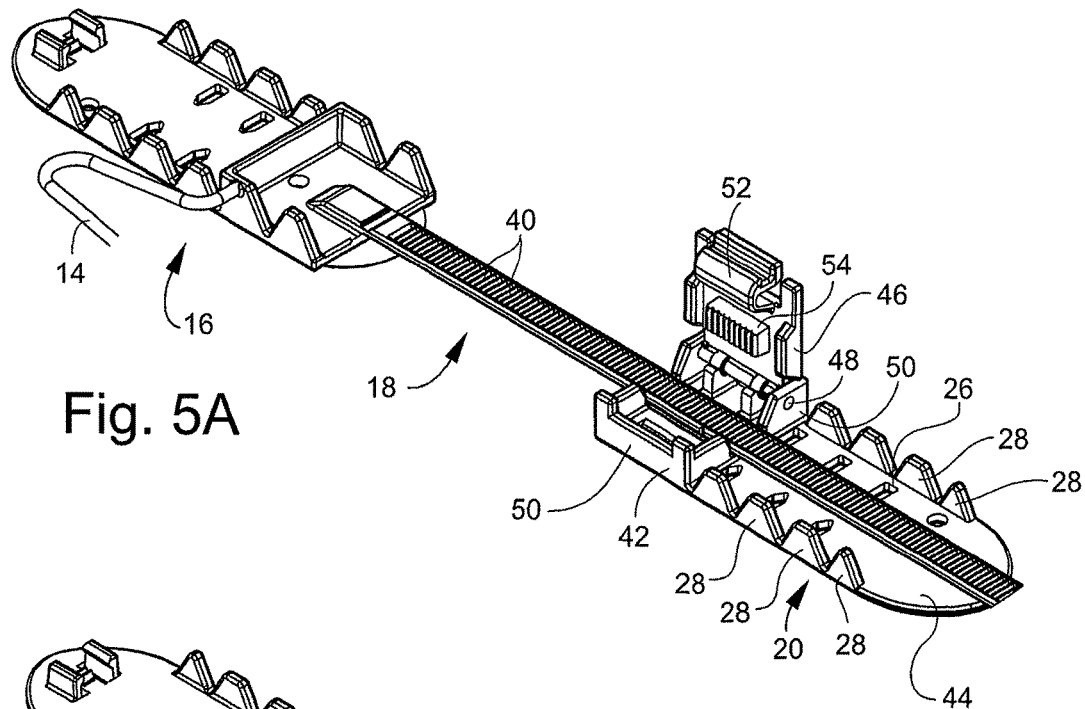
FIGS. 5A and 5B illustrate one embodiment of the lock mechanism in an open position and a closed position, respectively.
Figure 5B:
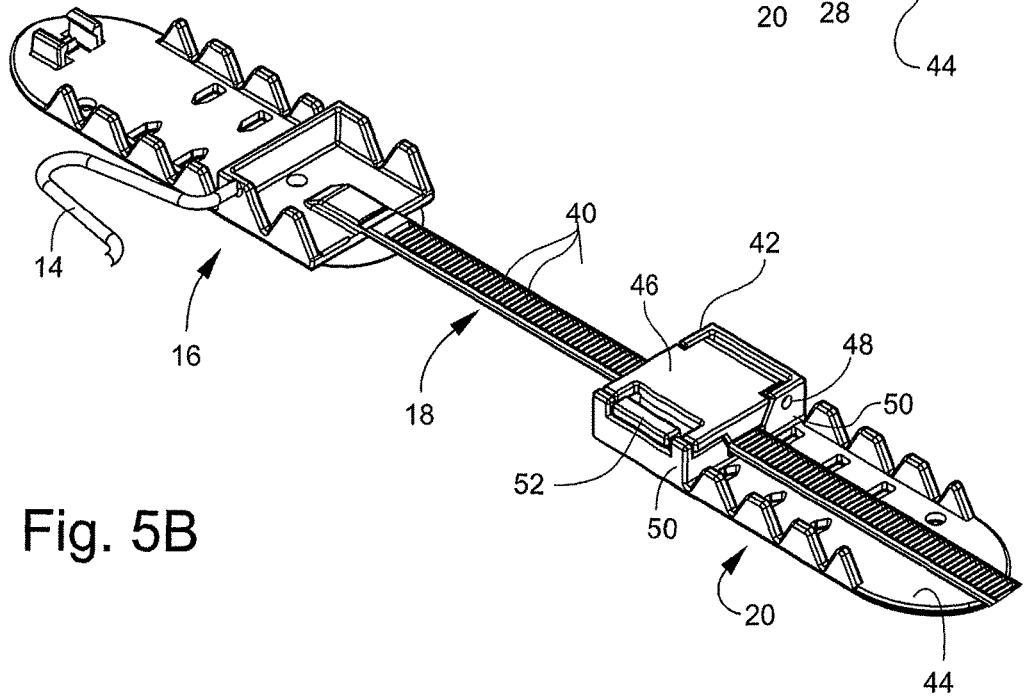

Lock member 20, see FIGS. 5A and 5B, may be slidably releasable on strap 18. Lock member 18 may be slid along strap 18 to facilitate closure and access to the wound. Lock member generally includes a locking mechanism 42 for releasably engaging strap 18. In one embodiment, the lock member 20 may include a bottom plate 44 with the locking mechanism 42 joined to an upper surface of the bottom plate 44.

Lock member 20 optionally includes at least one pair of staple holes 26 through the bottom plate 44. Any number of pairs of staple holes may be used, for example, 1-4 pairs of staple holes including any whole number between 1 and 4. The staple holes 26 may be used so that the base member may be stapled to the skin surrounding the wound. The base member may also optionally include at least one pair of staple guides (e.g., teeth) 28, for example, upstanding from the lateral edges of the bottom plate 44. Additionally, the staple guides 28 allow the lock member 20 to be more flexible therebetween. Any number of pairs of staple guides may be used, for example, 1-6 pairs of staple guides including any whole number between 1 and 6.

The locking mechanism 42, in one embodiment, may include a foldable lid 46 mounted via a hinge 48 to wall 50. The lid 46 is movable from an open position, FIG. 5A, to a closed position, FIG. 5B. The lid 46 may include a clasp 52 which is releasably engagable with wall 50. Optionally, the lid 46 may include strap engagement member 54 for holding the strap in a non-slidable manner when the lid 46 is in the closed position. Optionally, the locking mechanism 42 may include a mechanism (not shown) so that when lid 46 is in the closed position, the strap 18 may be pulled therethrough, thereby closing the wound by drawing the base member 16 and lock member 20 together. This mechanism may only allow the strap to be pulled through in one direction and hold fast in the opposite direction.

Lock member 20 may include an adhesive for releasably securing lock member 20 to the skin adjacent the wound. In one embodiment, the adhesive may be affixed to a bottom surface of the bottom plate 44. The adhesive may be any adhesive suitable for releasably adhering the lock member 20 to the skin adjacent the wound. The adhesive may be a hydrocolloid dressing (for example, commercially available under such tradenames as Duoderm, Granuflex, Ultec, and 3M Tegaderm Hydrocolloid) and/or pressure sensitive adhesive. In one embodiment, the adhesive covers all or a portion of the bottom surface of bottom plate 44. In one embodiment, the adhesive may be protected, prior to use, by a release layer. In another embodiment, adhesive may include a mesh (not shown) throughout the adhesive and may extend beyond the peripheral edge of the adhesive. The adhesive may be positioned on the lock member 20 in the same fashion as the adhesive 32 is employed with the base member 16, and shown in FIG. 2A.

Figure 6:
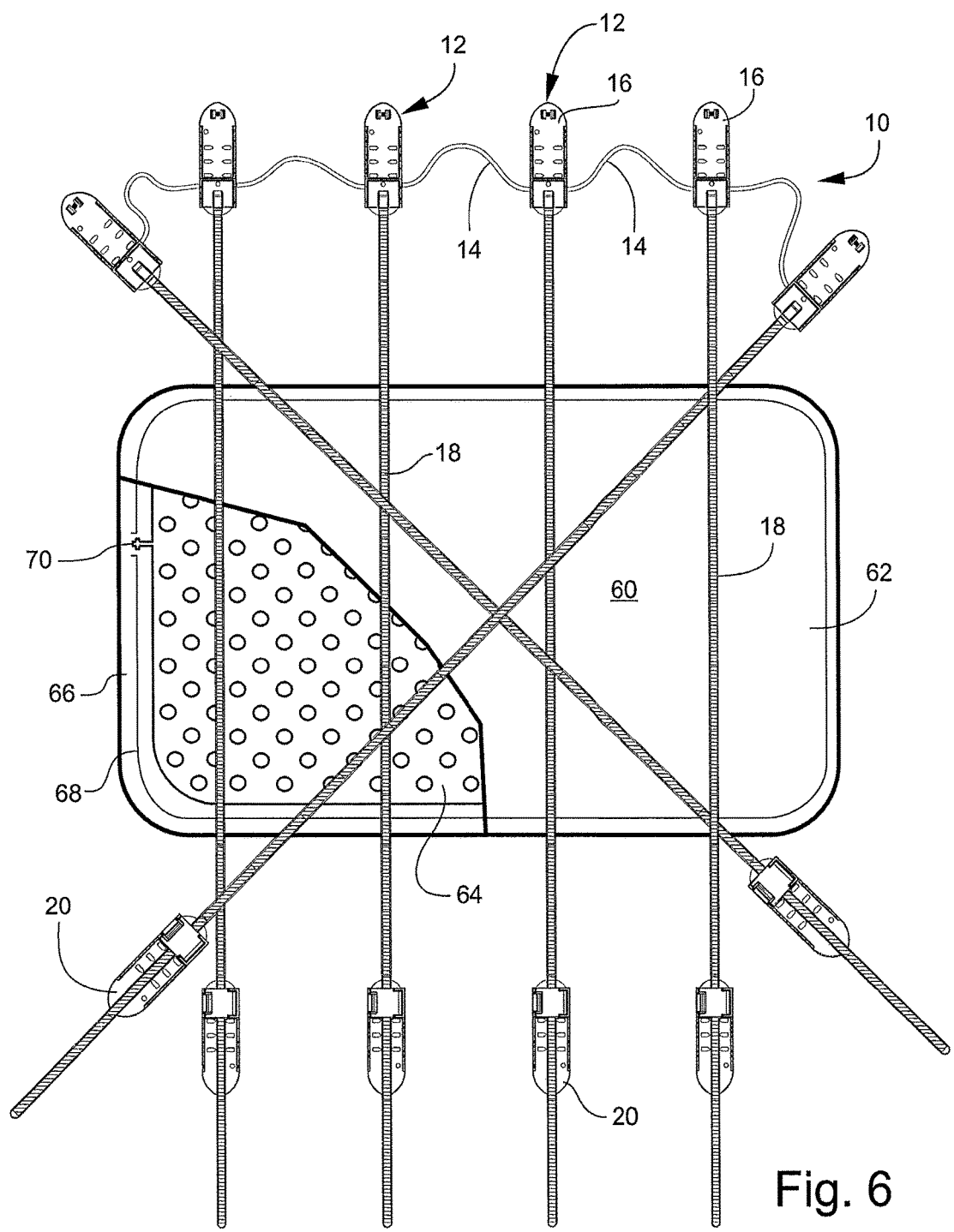
FIG. 6 is an illustration of the inventive system in operation along with an optional wound covering.

In operation, referring to FIG. 6, system 10 is removed from a sterile packaging (not shown). The system 10 is spread, as necessary, so that the base member 16 is on one side of the wound, the lock member 20 is on another side of the wound, and the strap 18 traverses the wound. With the locking mechanism 42 in the open position (FIG. 5A), the base member 16 and lock member 20 are affixed to the skin adjacent the wound, via the adhesive. Staples (not shown) may be used to further secure the base member 16 and lock member 20 to the skin adjacent the wound. Strap 18 is inserted into the open locking mechanism 42. The base member 16 and lock member 20 may be drawn together, whereby the wound may be closed (closure may only be sufficient to prevent internal organs from spilling from the wound during transportation, full closure of the wound may not be necessary or possible). Thereafter, the lock mechanism 42 may be closed (FIG. 5B), so that the strap 18 is fixed in place. Excess strap 18 (e.g., strap 18 extending beyond lock member 20) may be trimmed, as desired. If necessary to gain access to the wound after closure with system 10, the locking mechanism 42 may be released (FIG. 5A) for access and then reclosed (FIG. 5B).

Optionally, wound covering 60 may be included with system 10. Wound covering 60 adds, among other things, further protection to the wound. Wound covering 60 may also, without limitation, prevent ingress of contaminants into the wound, prevent spillage of internal organs from the wound, assist in retaining body heat, assist in retaining moisture that may escape from the wound, and provide a vehicle through which medicines and/or fluids may be administered to, or through, the wound. Wound covering 60 may be any size. For example, the wound covering 60 may have dimension of 12 inches by 12 inches by 3 mm.

Wound covering 60, in one embodiment, may be a laminate. The laminate may have at least two layers. A top layer 62 may be for preventing escape of heat and moisture through the wound and preventing ingress of contaminants to the wound. Top layer 60, in one embodiment, may be an aluminized plastic sheet. The aluminized surface faces toward or away from the wound. A middle layer 64 may be for administering fluids and/or medicines to the wound. Middle layer 64 may be a hydrophilic foam and/or an opened cell foam. Middle layer 64 may be affixed to top layer 62. Additionally, wound covering 60 may include a third layer. Bottom layer 66 may be a perforated plastic film, so that fluids and/or medicines fed into the middle layer 64 may be distributed into the wound. Top layer 62 may be joined to bottom layer 66 via a weld seam 68. Weld seam may be made by any suitable technique (for example, thermal weld, ultrasonic weld, adhesive, radio-frequency weld, and the like). Wound covering 60 may further include a fluid ingress port 70. Port 70 may be coupled with, for example, a saline bag (not shown). Port 70 is in fluid communication with middle layer 64 and extends beyond the weld line 68. Fluids and/or medicines may be administered from the saline bag through the port 70 to middle layer 64, and then into the wound from the middle layer 64 and through the bottom layer 66. Port 70 may be a luer lock-type device. Wound covering 60 may be supplied with system 10 folded and packaged in a sterile packaging or can be opened and worn on the inside of a battlefield helmet.

In operation, the wound covering 60 is spread over the wound, and then system 10 may be deployed as described above.

The system 10 may be compressed into a relatively small sterile package and is light-weight. Thus, it may be easily carried into a battlefield situation.

While, originally intended for short term closure, the system 10 may also have benefit in other surgical-type procedures, including, for example, any hospital/medical environment, such as an operating theater, emergency room, trauma center, or the like.

The present invention may be embodied in other forms without departing from the spirit and the essential attributes thereof, and, accordingly, reference should be made to the appended claims, rather than to the foregoing specification, as indicating the scope of the invention.

We claim:

1. A system for closure of a wound through skin comprising:
    at least two closure elements;
    each closure element including
        a base member securable directly to the skin,
        a strap being integral with the base member and being hingably connected to said base member, and
        a lock member slidably disposed on said strap and being lockable on said strap, and said lock member being securable directly to the skin; and
    a bent or curved and spreadable tether detachably connecting the base member of one closure element with the base member of another closure element, said tether being breakable or cuttable,
    wherein the system is spreadable around the wound with the base members on a first side of the wound, the lock members on another side of the wound, the straps traversing the wound, and the tether detachably connecting the at least two closure elements.

2. The system of claim 1 wherein said base member further comprises a strap fastener located on an upper surface of said base member, whereby said strap may be detachably engaged to said base member.

3. The system of claim 1 wherein said base member further comprises an adhesive located on a lower surface of said base member, whereby said adhesive may be attached to skin adjacent the wound.

4. The system of claim 1 wherein said base member has at least one pair of staple holes therethrough.

5. The system of claim 1 further comprising a hinge connecting said strap to said base member.

6. The system of claim 1 wherein said lock member further comprises an adhesive located on a lower surface of said lock member.

7. The system of claim 1 wherein said lock member has lock mechanism, whereby said strap may be releasably locked to said lock member.

8. The system of claim 1 wherein said lock member has at least one pair of staple holes therethrough.

9. The system of claim 1 further comprising a wound covering, whereby said wound covering is configured to be disposed between said straps and the wound.

10. The system of claim 9 wherein said wound covering being a laminate having at least two layers, a first layer being a moisture impervious layer adapted to contain body heat, and a second hydrophilic layer adapted to retain moisture.

11. The system of claim 1 wherein said tether is U or V shaped.

12. A system for closure of a wound through skin comprising:
    at least two closure elements;
    each closure element including
        a base member defining a plane, said base member being securable directly to the skin,
        a strap being integral with the base member and being affixed to said base member at an angle to said plane, and
        a lock member slidably disposed on said strap and being lockable on said strap, and said lock member being securable directly to the skin; and
    a bent or curved and spreadable tether detachably connecting the base member of one closure element with the base member of another closure element, said tether being breakable or cuttable,
    wherein the system is spreadable around the wound with the base members on a first side of the wound, the lock members on another side of the wound, the straps traversing the wound, and the tether detachably connecting the at least two closure elements.

13. The system of claim 12 wherein said base member further comprises a strap fastener located on an upper surface of said base member, whereby said strap may be detachably engaged to said base member.

14. The system of claim 12 wherein said base member further comprises an adhesive located on a lower surface of said base member, whereby said adhesive may be attached to skin adjacent the wound.

15. The system of claim 12 wherein said base member has at least one pair of staple holes therethrough.

16. The system of claim 12 further comprising a hinge connecting said strap to said base member.

17. The system of claim 12 wherein said lock member further comprises an adhesive located on a lower surface of said lock member.

18. The system of claim 12 wherein said lock member has lock mechanism, whereby said strap may be releasably locked to said lock member.

19. The system of claim 12 wherein said lock member has at least one pair of staple holes therethrough.

20. The system of claim 12 further comprising a wound covering, whereby said wound covering is configured to be disposed between said straps and the wound.

21. The system of claim 20 wherein said wound covering being a laminate having at least two layers, a first layer being a moisture impervious layer adapted to contain body heat, and a second hydrophilic layer adapted to retain moisture.

22. The system of claim 12 wherein said tether is U or V shaped.

* * * * *